United States Patent
Simnacher et al.

(10) Patent No.: US 8,455,210 B2
(45) Date of Patent: Jun. 4, 2013

(54) **BIOCHIP, AND METHOD FOR THE SELECTIVE IDENTIFICATION OF *CHLAMYDIA TRACHOMATIS* INFECTIONS**

(75) Inventors: Ulrike Simnacher, Ulm (DE); Vera Forsbach-Birk, Ulm (DE); Andreas Essig, Ulm (DE); Klaus-Ingmar Pfrepper, München (DE)

(73) Assignee: Mikrogen GmbH, Neuried (DE)

( * ) Notice: Subject to any disclaimer, the term of this patent is extended or adjusted under 35 U.S.C. 154(b) by 0 days.

(21) Appl. No.: 12/527,388

(22) PCT Filed: Mar. 7, 2008

(86) PCT No.: PCT/EP2008/001847
§ 371 (c)(1),
(2), (4) Date: Sep. 8, 2009

(87) PCT Pub. No.: WO2008/107203
PCT Pub. Date: Sep. 12, 2008

(65) Prior Publication Data
US 2010/0143952 A1    Jun. 10, 2010

(30) Foreign Application Priority Data

Mar. 7, 2007  (EP) .................................... 07004665

(51) Int. Cl.
| | |
|---|---|
| G01N 33/554 | (2006.01) |
| G01N 33/53 | (2006.01) |
| A61K 39/00 | (2006.01) |
| A61K 39/02 | (2006.01) |
| A61K 39/118 | (2006.01) |

(52) U.S. Cl.
USPC ............... 435/7.32; 424/184.1; 424/190.1; 424/263.1; 435/7.1; 435/7.2

(58) Field of Classification Search
None
See application file for complete search history.

(56) References Cited

U.S. PATENT DOCUMENTS

2009/0304722 A1*  12/2009  Theisen et al. ............. 424/184.1

FOREIGN PATENT DOCUMENTS

| WO | WO 02/08267 A2 * | 1/2002 |
|---|---|---|
| WO | WO/2004/074318 | 9/2004 |
| WO | WO 2006/045308 A2 * | 5/2006 |
| WO | WO/2007/110700 | 10/2007 |

OTHER PUBLICATIONS

Accession # O84100, UniprotKB/Swiss-Prot database: amino acid sequence of CT_098, 1998.*
Accession # O84462, UniprotKB/Swiss-Prot database: amino acid sequence of CT_456 TARP, 1998.*
Accession # O84608, UniprotKB/Swiss-Prot database: amino acid sequence of CT_603, 1998.*
Cruse et al. Illustrated Dict. of Immunology, 2nd ed., CRC Press, 2003, p. 46, 166, 382.*
Colman et al. Research in Immunology 145: 33-36, 1994.*
Definition of kit: Oxford Dictionaries. http://oxforddictionaries.com/definition/kit?q=kit Retrieved Feb. 20, 2012.*
Jyotika, et al. "Profiling of Human Antibody Responses to *Chlamydia trachomatis* Urogenital Tract Infection Using Microplates Arrayed with 156 Chlamydial Fusion Proteins", Infection and Immunity, vol. 74 (3), pp. 1490-1499 (Mar. 2006).
Sanchez-Campillo, et al. "Identification of Immunoreactive Proteins of *Chlamydia trachomatis* by Western Blot Analysis of a Two-Dimensional Electrophoresis Map with Patient Sera", Electrophoresis, vol. 20 (11), pp. 2269-2279 (Aug. 1999).
Biendo, et al. "Limits of the Microimmunofluorescence Test and Advantages of Immunoblotting in the Diagnosis of Chlamydiosis", Clinical and Diagnostic Laboratory Immunology, American Society for Microbiology , vol. 3 (6), pp. 706-709 (Nov. 1996).
Mikrogen GMBH: Product Information from http://www.mikrogen.de/download/PIRLCYD.pdf/ (Jan. 2006) (XP002451850).
Mikrogen Forum, "Zur Bedeutung von Chlamydien-Infektionen; recomLine Chlamydia Produkt-Prasentation", vol. 4 (15) (Nov. 2005) (XP002486262).

* cited by examiner

*Primary Examiner* — Oluwatosin Ogunbiyi
(74) *Attorney, Agent, or Firm* — Chalin A. Smith; Smith Patent Consulting

(57) ABSTRACT

The present invention relates to a method for the selective identification of *Chlamydia trachomatis* infections wherein the antigens CT017, CT098, CT318-L1 P, CT431-TARP, CT603-TSAP, and CT664 are used for the specific identification of *Chlamydia trachomatis* antibodies in samples from mammals. The method according to the invention facilitates the selective identification method of identification of *Chlamydia trachomatis* infections, in which no false positive results are generated by other *Chlamydia* species such as, for example, *Chlamydia pneumoniae*. The invention further relates to a biochip which has the aforementioned *Chlamydia trachomatis*-specific antigens for the identification of antibodies. The biochip with antigens according to the invention is suitable for multiparameter identification methods in particular.

10 Claims, No Drawings

BIOCHIP, AND METHOD FOR THE SELECTIVE IDENTIFICATION OF *CHLAMYDIA TRACHOMATIS* INFECTIONS

This application corresponds to the national phase of International Application No. PCT/EP2008/001847 filed Mar. 7, 2008, which, in turn, claims priority to European Patent Application No. 07.004665.1 filed Mar. 7, 2007, the contents of which are incorporated by reference herein in their entirety.

SEQUENCE LISTING

The instant application contains a Sequence Listing which has been submitted via EFS-Web and is hereby incorporated by reference in its entirety. Said ASCII copy, created on Dec. 3, 2009, is named LNK05400.txt, and is 37,448 bytes in size.

The present invention relates to a method for the selective detection of *Chlamydia trachomatis* infections, in which the antigens CT017, CT098, CT318-L1P, CT431, CT456-TARP, CT603-TSAP and CT664 are used for detecting *Chlamydia trachomatis*-specific antibodies in samples from mammals. In addition, the invention relates to a biochip, which has the aforementioned antigens for detecting the *Chlamydia trachomatis*-specific antibodies. The present invention also relates to a test kit that is suitable for detecting *Chlamydia trachomatis* infections.

Chlamydiae are infectious agents of global distribution and of considerable clinical and epidemiological relevance. They are obligate intracellular replicating bacteria, occurring morphologically and functionally in two different cellular forms (highly infectious, metabolically inactive elementary bodies and intracellular reticulate bodies capable of replication) and go through a typical development cycle. The target cells of the pathogens are as a rule the epithelial cells of the conjunctiva and of the mucosae of the respiratory tract and genital tract.

The reservoir for *Chlamydia trachomatis* and *Chlamydia pneumoniae* (new nomenclature also: *Chlamydophila pneumoniae*) is humans, whereas for *Chlamydia psittaci* (new nomenclature also: *Chlamydophila psittaci*) it is mainly birds, although economically useful animals can also be important sources of infection. Owing to their intracellular localization, chlamydiae have developed strategies for evading the host's defenses, so that development of chronic infection with the risk of secondary diseases is not rare. In such cases diagnosis by detection of the pathogen is generally no longer possible, whereas the detection of species-specific antibodies is acquiring considerable diagnostic importance.

Chlamydiae can also multiply in cells of the host's defense system, such as monocytes and lymphocytes. Possibly in this way the pathogens succeed in spreading from the site of the primary infection and thus reach other compartments (joints, vessels). The progress of the primary infection is clinically often uncharacteristic and oligosymptomatic, favoring the expansion and spread of the infection. As a primary infection evidently does not induce complete immunity, reinfections are by no means rare in the case of *Chlamydia pneumoniae* and *Chlamydia trachomatis*. Accordingly the therapy is often prolonged and is only successful with antibiotics that reach high intracellular levels of the active substance. Precisely because of their uncharacteristic clinical symptomatology, laboratory diagnostics play a decisive role in the detection of chlamydial infections.

In the industrial nations, *Chlamydia trachomatis* is among the commonest causes of sexually transmitted diseases (STD). According to estimates of the US "Center of Disease Control and Prevention" more than 700 million people are infected with *Chlamydia trachomatis*. The annual incidence is around 50 million. In the whole of Germany, an annual incidence of 300 000 is anticipated (altogether approx. 1.15 million). In developing countries the pathogen causes trachoma, a chronic keratoconjunctivitis, which is still the commonest cause of avoidable blindness in these countries.

The disease spectrum of *Chlamydia trachomatis* is dependent on the serotype of the pathogen. Serotypes A-C cause trachoma, serotypes L1-L3 cause lymphogranuloma venereum, an invasive sexually transmitted disease that progresses in stages, occurring primarily in the tropics. In contrast, serotypes D-K play the decisive role in the industrial nations as the cause of urogenital infections, which can lead to sterility resulting from infection and to postinfectious arthritis. The perinatal transmission of the pathogen from the infected mother to the neonate leads to so-called neonatal conjunctivitis or even to neonatal pneumonia. In view of the serious secondary diseases that can be caused by unrecognized and therefore untreated infections with *Chlamydia trachomatis*, screening is offered for high-risk groups in Scandinavian and Anglo-American countries. It is unclear at present whether screening should also be introduced in Germany.

*Chlamydia pneumoniae* is a pathogen that was unknown until about 15 years ago, and typically can cause respiratory tract infections such as sinusitis, pharyngitis, bronchitis and pneumonia. Seroepidemiological studies indicate that *Chlamydia pneumoniae* is widespread, with antibody prevalences of more than 50%. However, the clinical relevance of *Chlamydia pneumoniae* has not been elucidated conclusively. Within the scope of the competence network of the BMBF (Federal Ministry of Education and Research) "Community-acquired pneumonia" (CAPNETZ) efforts are currently being directed at elucidating the importance of the pathogen in community-acquired pneumoniae, although this is proving extremely problematic owing to difficulties with the methods used in laboratory diagnostics, especially in serology. It is, however, even more difficult to assess the relevance of the pathogen in extrapulmonary diseases. A key question, which is also of importance for health policy and the national economy, is whether *Chlamydia pneumoniae* is involved in atherogenesis and so is partly responsible for the widespread diseases of myocardial infarction and stroke.

*Chlamydia psittaci* is the causative agent of ornithosis or parrot fever (psittacosis). This is a zooanthroponosis, which as a rule is transmitted to humans in the air or less commonly by direct contact, from infected ornamental birds or domestic fowl through excretion of pathogen-containing secretions and excrement. Those at risk of infection include, in addition to keepers of ornamental birds and domestic fowl, mainly animal handlers and those employed in the fowl processing industry. On the whole, the disease has become rare in Germany, although owing to the difficulty of diagnosis we must assume a relatively high number of undetected cases.

The main form of manifestation of the infection is an atypical pneumonia, which can be accompanied by severe systemic symptoms. The infection can prove fatal if untreated. Transmission from person to person has not been observed to date, but the pathogen is regarded as highly contagious and is classified in laboratory safety category 3 according to the biomaterials regulations.

Moreover, *Chlamydia psittaci* is of considerable economic importance in the area of animal husbandry, where severe systemic infections can occur and abortion rates are high in infected stock, especially in sheep but also other domestic animals.

The diagnosis of chlamydial infections is generally difficult, time-consuming and expensive. To date, no sufficiently sensitive, standardized and easily evaluated methods of detection, which in addition do not produce any false-positive results, are available for the detection of chronic *Chlamydia trachomatis* infections.

Until now, a *Chlamydia trachomatis* infection has, for example, been detected with nucleic acid amplification tests (NAAT). These methods were used routinely in clinical laboratories for detecting genital infections. These commercially available assays are, however, very expensive and too complex for use on a large scale. Precisely because of the high selectivity of this test method, there is a risk of cross-contamination or false test results through incorrect handling of the samples. Therefore this test method requires considerable attention with respect to quality control and the training of laboratory personnel.

Moreover, there is a risk that the pathogen or its nucleic acid sequence will change and detection will no longer be possible with the existing probes. There is in addition a risk that false-positive results will be generated, if more than one chlamydia species has the probe's nucleic acid sequence.

Another known method is based on the detection of serum antibodies to *Chlamydia trachomatis*. The currently marketed genus-specific antibody detection systems detect antibodies to all chlamydia species and, in view of the high prevalence of *Chlamydia pneumoniae*-antibody positive patients, are often very difficult to interpret. Species-specific tests are technically very expensive and difficult to assess (microimmunofluorescence test).

In the past there have already been many unsuccessful attempts to identify immunodominant and specific chlamydia antigens. In particular, species-specific diagnosis by means of *Chlamydia pneumoniae* antigens has proved difficult. There were discrepancies in reactivity between MIF (microimmunofluorescence test), accepted as the gold standard until now, and the recombinant antigens (Maile et al., 2005, "recomLine *Chlamydia*: a new serological test system for the detection of antibodies against *Chlamydia trachomatis, Chlamydia pneumoniae* and *Chlamydia psittaci*", 3rd German Chlamydia Workshop, Sep. 3-Nov. 3, 2005, Jena).

WO 2004/074318 describes polypeptides of *Chlamydia trachomatis, Chlamydia psittaci* and *Chlamydia pneumoniae* and use thereof in diagnostics. Among more than 10 different polypeptides that are to be used for the diagnosis of *Chlamydia trachomatis*, protein CT664 is mentioned, among others.

Sharma et al., Infection and Immunity (March 2006), p. 1490-1499 describe the expression of 156 *Chlamydia trachomatis* fusion proteins that were used in microtiter plates for the diagnosis of urogenital infections with *C. trachomatis*. Although protein CT431 is mentioned in this publication in a list of 156 proteins, this antigen did not display significant reactivity with the sera investigated. This literature reference prefers the use of other antigens for diagnosis.

Sanchez-Campillo, Electrophoresis (1999), p. 2269-2279 describes the identification of immunoreactive proteins from *Chlamydia trachomatis* by Western Blot analysis and two-dimensional gel electrophoresis with patient sera. The method described there is unsuitable for routine diagnostics, as it is too laborious and too expensive.

Biendo et al., Clinical and Diagnostic Laboratory Immunology (November 1996), p. 706-709 describe the limitations of the microimmunofluorescence test and the advantages of immunoblotting in the diagnosis of chlamydia infections.

Initial tests within the scope of the present invention for the cloning and recombinant production of known chlamydia proteins, as for example the PGP3 proteins (Maile et al., 2004, "Evaluation of selected recombinant chlamydial antigens for serological diagnosis of *Chlamydia trachomatis* and *Chlamydia pneumoniae* infection", 5th Meeting of the European Society for Chlamydia Research, Jan.-Apr. 9, 2004, Budapest), MOMP, OMP2, hsp60, MIP and MOMPIV of *Chlamydia trachomatis* were not suitable for the development of a specific method of detection for *Chlamydia trachomatis* infections.

This shows that with whole-cell lysate antigens based on purified chlamydia elementary bodies it is not possible to achieve any substantial progress in chlamydia serodiagnostics. Thus, to date, no specific antigens of *Chlamydia pneumoniae* are known that permit reliable serological differentiation of *Chlamydia pneumoniae* and *Chlamydia trachomatis* infections.

Furthermore, a great many PCR-based methods were developed, in which for example different target genes of *Chlamydia pneumoniae* from respiratory and nonrespiratory specimens were developed. Many of these PCR methods were not, however, sufficiently reliable or stable to provide reproducible results in routine clinical investigations. Therefore these assays were instead used as research tools.

In addition, methods based on enzyme immunoassay were used for detecting *Chlamydia trachomatis* infections by means of monoclonal or polyclonal antibodies. So far, however, these tests have not proved successful, especially owing to their low sensitivity and the false-positive test results that they produce.

One problem of the present invention is therefore to provide a selective method of detection for *Chlamydia trachomatis* infections. Said method should have no cross-reactivity with respect to other pathogens and therefore should in particular provide demarcation from *Chlamydia pneumoniae* infections.

Another problem of the present invention is to establish, in the diagnosis, which type of chlamydial infection is involved. The possibilities include acute infection with *Chlamydia pneumoniae* or chronic infection with *Chlamydia trachomatis* and acute *C. trachomatis* infection. Another problem of the present invention is to provide highly specific and/or highly sensitive antigens for the differential diagnosis of chlamydia infections.

In particular the test method must have high sensitivity, to make it possible to detect chronic *Chlamydia trachomatis* infections. Furthermore, the test method should be suitable for the selective detection of *Chlamydia trachomatis* infections for routine laboratory investigations on the basis of cost-effective, simple and reliable handling and in addition be suitable not only for detecting the causative agent of the disease, but also for assessing the progression of the disease or the disease stage.

The selective test method should in particular be suitable for use in multiparameter tests based on biochip or Luminex technology, especially as chlamydial infections can also be the trigger of clinical pictures with typical subsequent complications such as reactive arthritis. The diagnosis of arthritis at present involves considerable expense for individual tests, owing to the need to find the precise cause among many potential pathogens.

Another problem is to provide a test method for the veterinary medical area, where there is also a great demand for selective tests.

The problem according to the invention was solved by using individually immobilized recombinant antigens instead of the lysates and elementary bodies used conventionally, and represents a substantial improvement in the area of chlamydia serodiagnostics. The identification of the antigens specific to *Chlamydia trachomatis* is illustrated in the examples.

The successful characterization of immunodominant and species-specific chlamydia proteins, which can be used as antigens for diagnostics, could be achieved, unexpectedly, through exclusive in-vivo expression, wherein antigens were identified that evade the conventional diagnostic assays. In this, all antigens were identified by 2D-immuno-electrophoresis and Western Blots by means of characterized patient sera and subsequent mass-spectrometric analysis of reactive spots. This is also described in the examples.

The advantageously high seroreactivity of the antigens according to the invention was achieved in that the candidate antigens were cloned in bacterial expression vectors and were expressed recombinantly and after optional optimization of expression and protein purification in line assays, they were analyzed in order to find an optimal combination of recombinant antigens. In the "line assays", several antigens, generally produced recombinantly, are applied as narrow bands on a suitable support (for example nitrocellulose) and the test strips are reacted with the test fluid (for example serum). These antigens make possible, advantageously, on the one hand precise species differentiation and on the other hand distinguishing between active and past chlamydial infections. Previously this was only possible with PCR methods.

Stage-dependent, species-specific serology for the diagnosis of *Chlamydia trachomatis* infections has an important role in therapeutic decisions but also in assessing the prognosis of existing conditions.

As already mentioned, use of the antigens according to the invention in a multiparameter method advantageously makes possible the simultaneous detection of various pathogens, in particular detection of the various causative agents of chlamydia, *Chlamydia trachomatis*, *Chlamydia pneumoniae* and *Chlamydia psittaci*. One advantage of using more than one antigen in the detection method is that test reliability is increased. The antigens according to the invention possess on the one hand greater specificity in the case of clinically relevant infections with *Chlamydia trachomatis*, and on the other hand less cross-reactivity with *Chlamydia pneumoniae* than the previously known antigens produced recombinantly (see Table 3). The antigens according to the invention were not previously known in connection with the selective detection of *Chlamydia trachomatis*.

The antigen CT456-TARP had indeed already been described (Clifton et al., Proc Natl Acad Sci USA. 2004, Jul. 6; 101 (27): 10166-71; Clifton et al., Infect Immun. 2005, July; 73(7):3860-8; Jewett et al., Proc Natl Acad Sci USA. 2006 Oct. 17; 103(42): 15599-604.), but not in connection with the detection of *Chlamydia trachomatis*. It was established within the scope of the present invention that it is a highly specific and highly sensitive antigen, which is especially suitable for the differential diagnosis of chlamydia infections.

Some other immunoreactive antigens of *Chlamydia trachomatis* had already been described: CT858-CPAF (Sharma et al., Infect Immun. 72(12):7164-71); CT089 and CT795 (Sharma et al., Infect Immun. 74(3): 1490-99) and CT813 (Chen et al., Infect Immun. 74(8):4826-40). These four proteins were investigated for purposes of comparison within the scope of the present application (Table 3). The results show that the four known antigens CT858-CPAF, CT089, CT795 and CT813 in infections with *Chlamydia pneumoniae* and in healthy blood donors, react with antibodies to *Chlamydia trachomatis* more frequently than the antigens according to the invention (see Table 3).

The present invention therefore relates to a method for the selective detection of *Chlamydia trachomatis* infections, the antigens being selected from the group comprising: CT017, CT098, CT318-L1P, CT431, CT456-TARP, CT603-TSAP and CT664, and additionally preferably also from fragments and partial sequences of the above antigens or from antigens essentially identical to them, which are used for detecting antibodies in samples. Preferably at least two, more preferably at least three, even more preferably at least four, more preferably at least five and most preferably at least six antigens are selected from the aforementioned groups of antigens. More preferably the antigens are selected from the group comprising: CT017, CT098, CT318-L1P, CT431, CT603-TSAP and CT664.

In a preferred embodiment of the invention for the detection of chronic diseases, the antigens are especially preferably selected from the group comprising: CT017, CT098, CT318-L1P, CT431, CT603-TSAP and CT664. Even more preferably for the detection of chronic diseases or infections, the antigens are selected from the group comprising: CT017, CT098, CT318-L1P and CT664. Most preferably the antigens are: CT603-TSAP and CT664.

In the method according to the invention and in the test kits or biochips, either the complete or almost complete polypeptides can be used. However, it is also possible to use fragments thereof in the tests. To establish which fragments are especially suitable for the immunological tests, it is first established, based on the three-dimensional structure of the polypeptide or on the basis of hydrophilicity/hydrophobicity blots, which regions of the polypeptide are located on the surface and are therefore in contact with the immune system of the host organism. These fragments are then prepared in segments of at least 15, preferably at least 20, more preferably at least 30 and especially preferably at least 50 amino acids. They can be prepared either by chemical synthesis or recombinantly by expression, for example as a fusion polypeptide with an immunologically inactive carrier protein. These fragments are then reacted in suitable tests, for example so-called line assays, ELISA tests or Western blots with various sera that have been characterized as precisely as possible, for which it is known what infection is present. It is a matter of precise determination of the pathogen and the present state of the infection (acute, long past or chronic). Based on the test results, it is then possible to decide which of these fragments are suitable, very suitable, especially suitable or unsuitable for use in the diagnostic test method.

Another embodiment of the invention relates to a method that is characterized in that the detection of the antibodies comprises the detection of an antigen/antibody complex. A preferred embodiment of the invention relates to an in-vitro method of analysis of samples from human patients. In a preferred embodiment of the method, the samples to be investigated are submitted to cell lysis, before being brought into contact with the antigens. In this way pathogens, or pathogen-specific antigens are released from the infected cells.

In another preferred embodiment of the method, the antibodies are detected by ELISA (enzyme-linked immunosorbent assay), Western Blot or line assay, especially preferably ELISA. It is especially preferable to use ELISA, Western Blot and line assay with peroxidase-conjugated secondary antibodies, with detection of the antigen-antibody reaction by means of a staining substrate (TMB, tetramethylbenzidine).

Another preferred embodiment of the method is characterized in that in the method for the selective detection of *Chlamydia trachomatis* infections the quantity of antibodies in the sample is determined quantitatively.

In a preferred embodiment of the method, the antigen-antibody reaction is detected using peroxidase-conjugated secondary antibodies and the staining substrate (TMB).

Another embodiment of the invention relates to a method of analysis of the course of a *Chlamydia trachomatis* infection, in which samples are taken from a patient at defined time intervals and the samples are investigated by the method according to the invention. Preferably, in the method according to the invention for the selective detection of *Chlamydia trachomatis* infections, the quantity of antibodies in the sample is determined quantitatively.

Furthermore, the invention relates to a test kit for the selective detection of *Chlamydia trachomatis* infections, characterized in that antigens, selected from the group comprising: CT017, CT098, CT318-L1P, CT431, CT456-TARP, CT603-TSAP, and CT664, are used for detecting antibodies in samples from patients. At least two, more preferably at least four, and most preferably at least six antigens are selected from the aforementioned groups of antigens. In an especially preferred embodiment the entire group of *Chlamydia trachomatis*-specific antigens is used for the detection method.

In addition, the invention relates to a biochip that contains antigens, selected from the group comprising: CT017, CT098, CT318-L1P, CT431, CT456-TARP, CT603-TSAP, and CT664, for the detection of *Chlamydia trachomatis*-specific antibodies. At least two, preferably at least four, and most preferably at least six antigens are selected from the aforementioned groups of antigens.

One embodiment of the biochip is characterized in that the antigens, selected from the group comprising: CT017, CT098, CT318-L1P, CT431, CT456-TARP, CT603-TSAP, and CT664, are applied on a site of a solid support, for example of glass or plastic or a membrane, preferably a membrane, and sites on the solid support with other antigens are spatially separated therefrom. It is further preferred that the antigen/antibody complexes can be detected or visualized by color reactions on the solid support, preferably a membrane. Preferably detection is carried out using color reactions, preferably with TMB (tetramethylbenzidine), or by means of fluorescent dyes such as preferably, Cy3 or Cy5 dye. It is especially preferred that a dye either binds to the antigen/antibody complex, or is intercalated into it. More preferably, spatially separated from the sites on the membrane with the antigens according to the invention, other antigens are applied, which make specific detection versus *Chlamydia pneumoniae* possible. For biochip applications with solid biochip surfaces (plastic), the use of Cy3, Cy5 dyes is especially preferred.

Biological samples are used for the detection method according to the invention. These biological samples contain the *Chlamydia trachomatis*-specific antibodies. The biological sample can originate from human or animal patients, preferably from human patients. The biological sample can be any sample that contains body fluid or tissue, for example blood or bone marrow. Serum or plasma is preferably used. It is additionally preferred for the samples to be submitted to cell lysis, before they are brought in contact with the antigens. Methods of sample preparation for immunoassays are known by a person skilled in the art. The preparation of the samples can comprise for example centrifugation, precipitation, concentration, filtration, dialysis or dilution of the sample. The type of sample preparation depends on the technique of detection of the antibodies.

The method according to the invention is based on usual techniques of molecular biology, microbiology, recombinant DNA, and immunology, known by a person skilled in the art. These techniques are described in detail in the literature. In connection to this, reference may be made in particular to: Molecular Cloning, A Laboratory Manual, second edition (1989); DNA Cloning, Volumes I and II (D. N. Glover, Ed., 1985); Oligonucleotide Synthesis (M. J. Gait, Ed, 1984); Nucleic Acid Hybridization (B. D. Hames & S. J. Higgins, Eds., 1984); Transcription and Translation (B. D. Hames & S. J. Higgins, Eds., 1984); Animal Cell Culture (R. I. Freshney, Ed., 1986); Immobilized Cells and Enzymes (IRL Press, 1986); B. Perbal, A Practical Guide to Molecular Cloning (1984); the series, Methods in Enzymology (Academic Press, Inc.); Gene Transfer Vectors for Mammalian Cells (J. H. Miller and M. P. Calos, Eds., 1987, Cold Spring Harbor Laboratory), Methods in Enzymology Vol. 154 and Vol. 155 (Wu and Grossman, or Wu), Mayer and Walker, Eds. (1987), Immunochemical Methods in Cell and Molecular Biology (Academic Press, London), Scopes, (1987), Protein Purification: Principles and Practice, second edition, (Springer-Verlag, N.Y.), and Handbook of Experimental Immunology, Volumes I-IV (D. M. Weir and C. C. Blackwell, eds, 1986).

The detection of a *Chlamydia trachomatis* infection takes place via the detection of *Chlamydia trachomatis*-specific antibodies in the samples by the antigens according to the invention. The term "antibody" denotes an immunoglobulin or a derivative thereof, which is able to bind to the antigens according to the invention.

The "antigens" according to the invention can bind to the *Chlamydia trachomatis*-specific antibodies. The invention relates to antigens with the sequences given in the sequence listings and additionally preferably also immunogenic fragments or partial sequences of the amino acid sequences shown in the sequence listings and additionally preferably also immunogenic antigens that are substantially identical to the amino acid sequences in the sequence listings.

Suitable fragments or partial sequences of the amino acid sequences of the antigens usually have a length of at least 15 amino acids, preferably at least 20 amino acids and more preferably at least 25 amino acids. Fragments of the antigens according to the invention that have at least one diagnostically relevant epitope are preferably used for the tests. Various methods for the mapping of antigens are known by a person skilled in the art. Using various methods of epitope mapping, it is possible to determine which regions are especially relevant for immunological diagnostics. Linear epitopes are located on short amino acid segments. Conformation epitopes arise through the spatial configuration of the antigen. Therefore preferred fragments, which have conformation epitopes, are as a rule longer, usually at least 50 amino acids, more preferably at least 75 amino acids. However, it is also known by a person skilled in the art that only a few amino acids are involved in the epitope. Other amino acids, located for example inside the antigen, can be altered without changing the diagnostic importance of the epitope.

The expression: "antigens that are substantially identical to the amino acid sequences in the sequence listings" encompasses amino acid sequences for which (for example by mutation) 1 to 20, preferably 1 to 15, more preferably 1 to 10, especially preferably 1 to 5, and most preferably 1 to 3 amino acids have been substituted, deleted or added, in comparison with the sequences in the sequence listings.

It is known by a person skilled in the art that the antigenic properties of a protein or polypeptide often are not altered if one or a few amino acids are altered at immunologically unimportant sites. Therefore amino acids can easily be altered if they have a similar character or do not affect, or do not substantially affect, the tertiary structure of the protein. Often, for example, exchange of Gly for Ala or vice versa does not affect the immunological character.

Suitable fragments or partial sequences or "substantially" identical antigens are proteins that display selectivity with respect to *Chlamydia trachomatis*-specific antibodies. Preferably, when carrying out a detection method according to the invention, in accordance with the examples using positive blood donor sera without clinically suspected chronic *C. trachomatis* infection, a false-positive result is obtained in at most 3 out of 6 persons, more preferably at most 2 out of 6 persons and even more preferably at most 1 out of 6 persons.

The antigens are selected from the group comprising CT017, CT098, CT318-L1P, CT431, CT456-TARP, CT603-TSAP and CT664 or fragments thereof. More preferably the antigens are selected from the group comprising: CT017, CT098, CT318-L1P, CT431, CT603-TSAP and CT664.

In a preferred embodiment for detecting chronic diseases, the antigens are especially preferably selected from the group comprising: CT017, CT098, CT318-L1P, CT431, CT603-TSAP and CT664. The antigens from the group comprising: CT017, CT098, CT318-L1P and CT664 are even more preferred for the detection of chronic diseases or infections. The antigens are most preferably: CT603-TSAP and CT664.

Table 1 shows the antigens according to the invention with their sequence numbers (SEQ ID NO), the sequences being shown in the sequence listing.

At least two, preferably at least four, and more preferably at least six antigens are selected from the aforementioned groups of antigens. In an especially preferred embodiment the entire group of *Chlamydia trachomatis*-specific antigens is used for the detection method.

In addition to the antigens stated above, other *Chlamydia trachomatis*-specific antigens can also be used in the detection method according to the invention. If the detection of the antigen/antibody complexes takes place selectively, other antigens against other pathogens can also be used additionally and simultaneously in the same detection method. For example, the antigen/antibody complexes of the various pathogens could be analyzed alongside one another on the basis of different spectroscopic properties.

TABLE 1

*Chlamydia trachomatis* antigens (The GenBank numbers are the numbers under which the complete genomes of two isolates of *Chlamydia trachomatis* can be found. So far there is no separate entry for the individual genes. These are distinguished on the basis of the number of the open reading frame with the prefix CT for *Chlamydia trachomatis* in the complete genome; however, the sequence listings are decisive):

| Antigen | SEQ ID NO | GenBank number |
|---|---|---|
| CT017 | 1 | NC000117 |
| CT098 | 2 | NC000117 |
| CT318-L1P | 3 | CP000051 |
| CT431 | 4 | NC000117 |
| CT456-TARP | 5 | NC000117 |
| C/603-TSAP | 6 | NC000117 |
| CT664 | 7 | NC000117 |

The antigens can be produced by known methods. In particular the antigens can be cloned in bacterial expression vectors and expressed recombinantly. Organisms suitable for this are known by a person skilled in the art and include for example the bacterium *Escherichia coli*. The production of the antigens is described in example 1.

The antibodies can preferably be detected by immunoassays. Either direct or indirect immunoassays can be used for this. These assays comprise, but are not restricted to: competitive binding assays, noncompetitive binding assays, radioimmunoassays, enzyme-linked immunosorbent assays (ELISA), Western Blot, line assay, sandwich assays, precipitation reactions, gel-diffusion-immunodiffusion assays, agglutination assays, fluorescence immunoassays, chemoluminescence immunoassays, immuno-PCR immunoassays, protein A or protein G immunoassays and immunoelectrophoresis assays.

The use of an enzyme-linked immunosorbent assay (ELISA), Western Blot or line assay is especially advantageous, more preferably ELISA. These methods are based on antigen-antibody interactions, where the resultant antigen/antibody complex can be detected by known detection methods. The use of ELISA methods, Western Blots and line assays with peroxidase-conjugated secondary antibodies is especially preferred, with detection of the antigen-antibody reaction via a staining substrate (TMB).

ELISA test methods in which the antigens are bound, generally noncovalently (hydrophobic interactions), to a solid phase and are brought in contact with a sample fluid, are especially suitable. A microtiter plate, for example, can be used as the solid phase. The protein (antigen) can then interact with the solid phase or the surface of the microtiter plate, usually made of polystyrene, e.g. at high pH value. Preferably a biochip is used as the solid phase.

Indicator systems for the detection of antigen/antibody complexes are known by a person skilled in the art. For example, after formation of the antigen/antibody complex, a second antibody can be used, which recognizes the constant part of the first antibody or in some other way binds specifically to the antigen/antibody complex. The second antibody or the compounds for detecting the antigen/antibody complex, for example a monoclonal or polyclonal antibody or a fragment thereof, preferably possesses a marker. Even more preferably it has a nonradioactive marker, for example an enzyme marker, fluorescence marker, light emission marker and so on. Especially preferably it has an enzyme marker such as an alkaline phosphatase, β-galactosidase or horseradish peroxidase.

The second antibody can for example be coupled to an alkaline phosphatase, the alkaline phosphatase then catalyzing an enzymatic chromogenic conversion. The colorless chromogen is then converted to a dye and measured. The amount of dye released is then correlated with the amount of the antibody that is sought. Other competitive or noncompetitive methods of measurement are known by a person skilled in the art.

Furthermore, compounds or markers for the direct detection of the antigen/antibody complex can also be used, for example radioactive, fluorescent biological or enzymatic tags. It is especially advantageous if the antigen/antibody complex is bound to the dye and the site on the membrane at which the antigen/antibody complex with the antigens according to the invention is applied can be detected. This makes possible the selective, simultaneous detection of different pathogens, for example *Chlamydia trachomatis* or *Chlamydia pneumoniae*. Preferably the test results can then be evaluated optically, wherein for example colored sites indicate the positive detection of the pathogens whose antigens were applied at that site. Moreover, it is preferable for the optically detectable antigen/antibody complexes to differ in color or in their wavelength absorption behavior. In this way, in addition to or instead of spatial characterization, the antigen/antibody complexes can further be characterized by their absorption behavior. The use of peroxidase-conjugated secondary antibodies, with detection of the antigen-antibody reaction via a staining substrate (TMB), or the use of fluorescent dyes such as Cy3 or Cy5, is preferred. All methods for detecting the antigen/antibody complex can be used both for the methods with and without a biochip or solid support.

Another embodiment of the invention comprises a test kit for the selective detection of *Chlamydia trachomatis* infections. The test kit comprises the aforementioned *Chlamydia trachomatis*-specific antigens. The number of different *Chlamydia trachomatis*-specific antigens described elsewhere is also suitable for the test kit. The execution of the method and the techniques for detecting the antigen/antibody complexes are applicable to the test kit. In particular the test kit can additionally contain the substances necessary for detection of the antigen/antibody complexes.

Furthermore, the test kit can additionally comprise other components such as washing buffers or compositions that contain a *Chlamydia trachomatis*-specific antibody as standard. Additionally, the test kit can also comprise a microtiter plate or a biochip, on which the antibodies are immobilized. Furthermore, the test kit can also contain information materials, for example instructions for use, which describe sample preparation and/or the specification for carrying out the assay.

One embodiment of the invention comprises a biochip, on which the antigens according to the invention are applied. The number of different *Chlamydia trachomatis*-specific antigens described elsewhere is also suitable for the method with a biochip. The execution of the method and the techniques for detecting the antigen/antibody complexes are also applicable to the method with a biochip. In particular the antigens can be applied to the membrane of the biochip.

For example porous, naturally occurring or synthetic polymers, glass, ceramic materials, cellulose materials or similar can be used for the membrane. The materials can be made into a membrane for example from films, fibers or particles (for example spherules, which are held together by adhesives or binders). Especially preferably, the membrane consists of polycarbonate, nitrocellulose, cellulose acetate, polyamide, polyester, polyvinylidene fluoride or nylon. Most preferably the membrane consists of nitrocellulose. The expression "nitrocellulose" refers to ester cellulose with nitrate groups. The expression "nitrocellulose" comprises in addition ester cellulose with nitrate groups alone or with a mixture of various esters, which were produced by acids other than nitrating acid, in particular aliphatic carbocyclic acids. The expression "applied" means that the antigens have sufficient affinity for the membrane or are even linked chemically to it, so that the application of the sample fluid or of any other washing and reaction solutions required does not lead to removal of said antigens.

The method according to the invention can be carried out as follows (see also examples):

The first step of the serological detection reaction is immobilization of the antigens on the solid support or the solid phase, for example the nitrocellulose membrane, the microtiter plate or the biochip. The antigens according to the invention or a selection from the group of antigens according to the invention are immobilized on the surface, for example by hydrophobic interactions.

After an optional washing step, the immobilized antigens are then brought in contact with the sample fluid. Sample preparation can be carried out by the methods described above and as explained in the examples, but is not restricted to this. As a result of the antigen/antibody interaction, the *Chlamydia trachomatis*-specific antibodies from the sample fluid are bound to the antigens according to the invention. Antigen/antibody complexes are formed.

After a suitable incubation time the solid support is washed to remove the residues of the sample. Then a solution for detecting the antigen/antibody complex is brought in contact with the antigen/antibody complexes, wherein quantitative or qualitative detection can take place, for example spectroscopically. For example, automated measurement of the depth of color of the chromogen can be carried out.

In one embodiment of the invention, the course of the *Chlamydia trachomatis* infection is evaluated. The test kit according to the invention or the biochip according to the invention can also be used for this embodiment of the method. At least two, more preferably at least three, even more preferably at least four and most preferably at least five samples from the same patient are tested at different time points and the presence of *Chlamydia trachomatis* or the quantity of *Chlamydia trachomatis*-specific antibodies is measured. This method can include the collecting of data over a specified period. The patients' samples can be taken at regular or irregular, preferably regular time points. The interval between the taking of two samples can be between a week and twelve months, preferably between two weeks and four months and more preferably between 4 and 6 weeks, in order to monitor the increase in titer. This method allows the progression of the *Chlamydia trachomatis* infection to be observed.

EXAMPLE 1

Identification of the Antigens According to the Invention

Identification and characterization of the *Chlamydia trachomatis*-specific antigens was carried out by 2D-gel electrophoresis and mass spectrometry.

For this, first an inducible gene expression database was prepared for *Chlamydia pneumoniae* and *Chlamydia trachomatis* in *Escherichia coli*. For this, sera from patients with clinically and microbiologically confirmed *Chlamydia pneumoniae* or *Chlamydia trachomatis* infections were pooled and pre-absorbed against in-vitro expressed chlamydia antigens. For this, lysates of *Chlamydia pneumoniae*-infected HeLa229 cells were prepared at various infection time points.

After colony plot analysis with the aforesaid pre-absorbed sera, the reactive clones are isolated and the cloned DNA fragments are sequenced. By comparing with the already recorded sequences of *Chlamydia trachomatis* and *Chlamydia pneumoniae*, the identity of the in-vivo expressed antigens could be clarified.

In detail, identification of the antigens took place as follows: *Chlamydia trachomatis* serovar D/UW-3/Cx was cultivated on HeLa 229; 48-72 h after infection the cells were harvested and homogenized. *Chlamydia trachomatis* was isolated from the cell residues in subsequent centrifugation steps. The elementary bodies of *Chlamydia trachomatis* obtained were lysed with detergents and treated ultrasonically. The first step of the 2D-immunoelectrophoresis was carried out with Ready IPG strips, pH 3-10, 11 cm (BioRad); then SDS-PAGE was carried out in a 10% polyacrylamide gel. The gels were blotted for Western Blots or stained with Commassie Brilliant Blue for nanoLC-ESI-MSMS analysis. The Western Blots were carried out with sera from patients with a clinical picture of chronic infection with *Chlamydia trachomatis* at a dilution of 1:125. Reactive spots were cut out of the stained and dried gels of the 2D-immunoelectrophoresis, and were analyzed by the nanoLC-ESI-MSMS method. During this, the proteins in the spots were digested with trypsin, desalted and concentrated. The nanoLC-ESI-MSMS analysis was carried out with the Esquire 3000 plus instrument (Bruker Daltronics). The proteins were identified by MS/MS ion search (Matrix Science) and the sequences were compared with publicly accessible databases.

The genomic sequences of all antigens were amplified by PCR and specific oligodeoxynucleotides as primers from the genomic DNA of *Chlamydia trachomatis* and the amplificates were purified. The purified amplificates were cleaved with suitable restriction endonucleases, whose cleavage sequences were contained in the PCR primers, purified by agarose-gel electrophoresis and ligated into the vectors pUC8 or pDS1, which had been cleaved with the same restriction endonucleases. Competent *Escherichia coli* were transformed with the ligation products. Positive clones were isolated and were characterized by restriction analysis and DNA sequencing. The antigens were expressed in *Escherichia coli*. The expression of the antigens was detected in SDS-PAGE with staining with Coomassie Brilliant Blue and in Western Blot with specific human sera from patients with antibodies to *Chlamydia trachomatis*. The antigens were then purified by chromatographic methods.

Table 2 shows the cloning data of the *Chlamydia trachomatis* antigens.

TABLE 2

Cloning data for *Chlamydia trachomatis* antigens:

| Antigen | Vector | RE | Insert [bp] | theoretical [kDa] | Expression [kDa] | Expression [amount] |
|---|---|---|---|---|---|---|
| CT017 | pDS1 | BamHI-PstI | 58-1299 | 46 | 48 | +++ |
| CT098 | pDS1 | SalI-PstI | 1-1707 | 64 | 66 | ++ |
| CT318-L1P | pDS1 | BamHI-SalI | 1-696 | 26 | 24 | +++ |
| CT431 | pUC8 | BamHI-PstI | 1-534 | 20 | 21 | ++ |
| CT456-TARP | pDS1 | BamHI-SalI | 1-3015 | 113 | >100 | ++ |
| CT603-TSAP | pDS1 | BamHI-PstI | 1-585 | 22 | 23 | +++ |
| CT664 | pDS1 | BamHI-Xho/SalI* | 1-2487 | 93 | ~100 | + |

The seroreactivity of the recombinant expressed proteins was verified with the same specific sera that were used for identification.

For individual recombinant proteins, epitope characterization was carried out, in order to identify and demarcate species-specific epitopes. This was carried out by subcloning of individual partial fragments and analysis of seroreactivity in Western Blot or by means of peptides produced in solid-phase synthesis and analysis of seroreactivity in line assay as a function of sequence homologies. The seroreactivity of the identified antigens and species-specific partial fragments or peptides was then analyzed in line assay, to find an optimal combination of the recombinant antigens, which makes possible, on the one hand, precise species differentiation, and on the other hand makes it possible to distinguish between active and past chlamydial infections.

In order to demonstrate that human antibodies to the antigens CT017, CT098, CT318-L1P, CT431, CT456-TARP, CT603-TSAP and CT664 occur in particular in chronic infections with *Chlamydia trachomatis*, the sera from 24 patients with clinically suspected chronic infection with *Chlamydia trachomatis*, and 6 sera from healthy blood donors with antibodies to *Chlamydia trachomatis*, but without suspected chronic infection with *Chlamydia trachomatis*, were compared.

The results were compared with the already described antigens MOMP, OMP2, Hsp60 and MIP from the recomLine Chlamydia and with 4 other antigens already described as serologically relevant (CT089, CT795, CT813 and CT858-CPAF). The results are presented in Table 3. It can be seen that the antigens CT017, CT089, CT318-L1P, CT431, CT603-TSAP and CT664 react in particular with sera from patients with clinically suspected chronic infection with *Chlamydia trachomatis* (CT017 at 45.8%; CT096 at 66.7%; CT318 at 58.3%; CT431 at 29.2%; CT603 at 25.0%; CT664 at 50.0%), but hardly at all with the sera from healthy blood donors with antibodies to *Chlamydia trachomatis*, but without suspected chronic infection (CT017 at 16.7%; CT096 at 16.7%; CT318 at 16.7%; CT431 at 16.7%; CT603 at 0.0%; CT664 at 0.0%). In contrast, the already known antigens MOMP, OMP2, Hsp60 and MIP are less suitable for distinguishing between patients with clinically suspected chronic infection with *Chlamydia trachomatis* (MOMP at 91.7%, OMP2 at 79.2%; HSP60 at 54.2%; MIP at 62.5%; CT089 at 70.8%; CT795 at 87.5%; CT813 at 95.8%; CT858 at 37.5%) and healthy blood donors with antibodies to *Chlamydia trachomatis*, but without suspected chronic infection with *Chlamydia trachomatis* (MOMP at 100.0%; OMP2 at 83.3%; HSP60 at 66.7%; MIP at 66.7%; CT089 at 33.3%; CT795 at 50.0%; CT813 at 100.0%; CT858 at 33.3%). The surprising advantageous results of the antigens according to the invention can thus be seen from a comparison of the right-hand and middle columns in Table 3.

Only 3 antigens attained, for all samples seropositive for *Chlamydia trachomatis* from both groups, a very high sensitivity of at least 90% based on all samples (CT456-TARP at 90.0%; MOMP at 93.3%; CT813 at 96.7%). The value is calculated for example for CT456-TARP as follows: 22+5=27 divided by 24+6=30→90%. However, both MOMP and CT813 reacted more frequently with the sera from healthy blood donors with antibodies to *Chlamydia trachomatis*, but without suspected chronic infection (CT813 at 100.0%; MOMP at 100.0%; for comparison, CT456-TARP at 83.3%), than with the sera from patients with clinically suspected chronic infection with *Chlamydia trachomatis* (CT813 at 95.8%; MOMP at 91.7%; CT456-TARP also at 95.8%). This means that CT456-TARP has better specificity for sera from patients with clinically suspected chronic infection with *Chlamydia trachomatis* than the already known antigens MOMP and CT813.

The antigens CT431, CT603 and CT664 have, additionally, less cross-reactivity for *Chlamydophila pneumoniae* than all the already known antigens.

The diagnostic use of the antigens CT017, CT098, CT318-L1P, CT431, CT456-TARP, CT603-TSAP and CT664 therefore permits significantly better differentiation between patients with clinically suspected chronic infection with *Chlamydia trachomatis* and healthy, but seropositive subjects, than is the case with the currently known antigens.

TABLE 3

Serological characterization of the *Chlamydia trachomatis* antigens according to the invention

| | C. pneumoniae-positive sera without suspected C. trachomatis infection n = 20 | | Sera from patients with clinically suspected chronic C. trachomatis infection n = 24 | | C. trachomatis-positive blood donor sera without clinically suspected chronic C. trachomatis infection n = 6 | |
|---|---|---|---|---|---|---|
| Antigen | n | % | n | % | n | % |
| CT017 | 4 | 20.0 | 11 | 45.8 | 1 | 16.7 |
| CT098 | 1 | 5.0 | 16 | 66.7 | 1 | 16.7 |
| CT318 | 4 | 20.0 | 14 | 58.3 | 1 | 16.7 |

TABLE 3-continued

Serological characterization of the Chlamydia trachomatis antigens according to the invention

| | C. pneumoniae-positive sera without suspected C. trachomatis infection n = 20 | | Sera from patients with clinically suspected chronic C. trachomatis infection n = 24 | | C. trachomatis-positive blood donor sera without clinically suspected chronic C. trachomatis infection n = 6 | |
|---|---|---|---|---|---|---|
| Antigen | n | % | n | % | n | % |
| CT431 | 0 | 0.0 | 7 | 29.2 | 1 | 16.7 |
| CT456 | 3 | 15.0 | 22 | 91.7 | 5 | 83.3 |
| CT603 | 0 | 0.0 | 6 | 25.0 | 0 | 0.0 |
| CT664 | 0 | 0.0 | 12 | 50.0 | 0 | 0.0 |
| MOMP | 1 | 5.0 | 22 | 91.7 | 6 | 100.0 |
| OMP2 | 2 | 10.0 | 19 | 79.2 | 5 | 83.3 |
| HSP60 | 3 | 15.0 | 13 | 54.2 | 4 | 66.7 |
| MIP | 3 | 15.0 | 15 | 62.5 | 4 | 66.7 |
| CT089 | 3 | 15.0 | 17 | 70.8 | 2 | 33.3 |
| CT795 | 2 | 10.0 | 21 | 87.5 | 3 | 50.0 |
| CT813 | 7 | 35.0 | 23 | 95.8 | 6 | 100.0 |
| CT858 | 1 | 5.0 | 9 | 37.5 | 2 | 33.3 |

EXAMPLE 2

Execution of the Test Method

The antigens were expressed in *Escherichia coli*, grown in shake flasks or in a fermenter. The bacteria were harvested by centrifugation and lysed by means of detergents and ultrasonic treatment. After that, the antigens were partly contained in "inclusion bodies" or were soluble. The antigens contained in "inclusion bodies" were solubilized with urea.

Next the antigens underwent stepwise purification using chromatographic methods, in particular anionic and cationic exchange. The purified antigens were applied, at dilutions found empirically, on a polyacrylamide gel and were separated according to size in the electric field. After gel electrophoresis, the antigens were blotted in the electric field onto a nitrocellulose membrane and thus immobilized on the membrane.

However, application on the membrane can also be carried out directly by spraying empirically determined dilutions of the purified antigens onto the nitrocellulose membrane. After blot transfer, the membranes were treated with a protein-containing solution, in order to saturate still unoccupied protein binding sites on the nitrocellulose membrane.

The membranes were then dried and cut into strips. One strip in each case was then incubated with human serum at a dilution of 1:250 overnight at room temperature with gentle shaking. During this, the antibodies in the patients' serum bind to the antigens immobilized on the nitrocellulose membrane.

The nitrocellulose membrane strips were then washed 3× and then incubated for 60 min with a secondary antibody, which had been conjugated with horseradish peroxidase.

Then the nitrocellulose membrane strips were washed again 3× and then treated with a TMB (tetramethylbenzidine) solution. At the sites at which antigens that had reacted with patients' antibodies were immobilized, dye was immediately precipitated onto the nitrocellulose membrane strip. The strips were then dried and the colorations were analyzed (Table 3).

EXAMPLE 3

Reactivity of Partial Sequences

A total of 22 peptides each of 20 amino acids were selected from the sequences of the antigens, synthesized and tested with *Chlamydia trachomatis*-positive sera in two experiments in ELISA (direct adsorption of the peptides on the microtiter plate or covalent binding to the microtiter plate). The sequences of the peptides, the positions in the whole proteins and the results are presented in Table 4. Per antigen, in each case at least one of these peptides reacted with at least one serum.

TABLE 4

| SEQ ID No. | Peptide | Position | Sequence | Absorptive binding (n = 5) | covalent binding *) (n = 5) |
|---|---|---|---|---|---|
| 8 | CT017-1 | P262-V281 | PAVEETPVVTKTEEQKVTTV | 0 | 1 |
| 9 | CT017-2 | M348-E367 | MESFYRDEQKKKRVLTGELE | 0 | n.d. |
| 10 | CT017-3 | V368-D387 | VYPHIVKNNPGDYLLKNGED | 0 | 1 |
| 11 | CT098-1 | S162-E181 | SQIDNKKIKNLDDYVGKVCE | 1 | 0 |
| 12 | CT098-2 | T252-V271 | TWKRIRHPSEMVELNQELEV | 0 | 2 |
| 13 | CT098-3 | Q289-V308 | QKEHNPWEDIEKKYPPGKRV | 0 | 1 |
| 14 | CT098-4 | F550-D570 | FLVHGGDAGHDAEEESSDRD | 0 | 2 |
| 15 | CT318-1 | M001-S020 | MTKHGKRIRGIQETYDLAKS | 1 | 1 |
| 16 | CT318-2 | I050-T069 | IDPRKSDQQIRGSVSLPHGT | 0 | 0 |
| 17 | CT318-3 | P138-R157 | PTPKAGTVTTDVVKTVAELR | 0 | 0 |
| 18 | CT431-1 | E005-I024 | EMMHKLQDVIDRKLLDSRRI | 0 | 0 |
| 19 | CT431-2 | A101-S120 | AVPGRRFATPHARIMIHQPS | 1 | 3 |
| 20 | CT431-3 | E152-M171 | EATGQSREVIEKAIDRDMWM | 1 | n.d. |
| 21 | CT-456-1 | T103-I122 | TSPDTSESSETSSTSSSDHI | 3 | n.d. |

TABLE 4-continued

| SEQ ID No. | Peptide | Position | Sequence | Absorptive binding (n = 5) | covalent binding *) (n = 5) |
|---|---|---|---|---|---|
| 22 | CT-456-2 | S273-A292 | SIGGSRTSGPENTSDGAAAA | 1 | 0 |
| 23 | CT-456-3 | S454-D473 | SQEASSGYTPSAWRRGHRV D | 1 | 2 |
| 24 | CT-456-4 | I569-A588 | INTNNQTDDINTTDKDSDGA | 0 | n.d. |
| 25 | CT-456-5 | T598-N617 | TESSSGDDSGSVSSSESDKN | 0 | 3 |
| 26 | CT-456-6 | S721-T740 | SSGDESGGVSSPSSESNKNT | 0 | n.d. |
| 27 | CT603-1 | G006-I025 | GRQAPDFSGKAVVCGEEKEI | 0 | n.d. |
| 28 | CT603-2 | A087-F106 | ARNAGGIEGTEYPLLADPSF | 0 | 3 |
| 29 | CT603-3 | N172-F191 | NWRSGERGMVPSEEGLKEY F | 0 | n.d. |

*) In covalent binding, not all peptides could be tested, as some could only be dissolved in 8M urea, but urea interferes with covalent binding.

EXAMPLE 4

Serological Characterization of the *C. trachomatis* Antigens: Sera that are Reactive with the Antigens Various sera were tested with a line test for chlamydia, and the results of the antigens were compared with the new antigens. It was found that all new antigens permit better discrimination between sera from patients with clinically relevant infections with *Chlamydia trachomatis* compared with sera from seropositive, but clinically unremarkable blood donors. The results are presented in Table 5.

The results shown in Table 5 largely correspond to the results in Table 3, but a quotient was formed from the individual values, which clarifies the informative value of the antigens.

TABLE 5

| Antigen | *C. pneumoniae*-positive sera without suspected *C. trachomatis* infection N = 20 | | Sera from patients with clinically suspected chronic *C. trachomatis* infection n = 24 | | *C. trachomatis*-positive blood donor sera without clinically suspected chronic *C. trachomatis* infection n = 6 | | Specificity for clinically relevant infections % |
|---|---|---|---|---|---|---|---|
| | N | % | n | % | N | % | |
| CT017 | 4 | 20.0 | 11 | 45.8 | 1 | 16.7 | 73.3 |
| CT098 | 1 | 5.0 | 16 | 66.7 | 1 | 16.7 | 80.0 |
| CT318 | 4 | 20.0 | 14 | 58.3 | 1 | 16.7 | 77.8 |
| CT431 | 0 | 0.0 | 7 | 29.2 | 1 | 16.7 | 63.6 |
| CT456 | 3 | 15.0 | 22 | 91.7 | 5 | 83.3 | 52.4 |
| CT603 | 0 | 0.0 | 6 | 25.0 | 0 | 0.0 | 100.0 |
| MOMP* | 1 | 5.0 | 22 | 91.7 | 6 | 100.0 | 47.8 |
| OMP2* | 2 | 10.0 | 19 | 79.2 | 5 | 83.3 | 48.7 |
| HSP60* | 3 | 15.0 | 13 | 54.2 | 4 | 66.7 | 44.8 |
| MIP* | 3 | 15.0 | 15 | 62.5 | 4 | 66.7 | 48.4 |

*The antigens MOMP, OMP2, HSP60 and MIP are used in the recomLine *Chlamydia* and are known from the prior art.

The specificity in clinically relevant infections was calculated as the quotient of the percentage of recognized sera from patients with clinically suspected chronic *C. trachomatis* infection and the sum of the percentages of the recognized sera from patients with clinically suspected chronic *C. trachomatis* infection and the *C. trachomatis*-positive blood donor sera without clinically suspected chronic *C. trachomatis* infection. All the new antigens have a higher specificity for clinically relevant infections (>50% compared with <50% for the already known antigens) than the already known antigens used in the recomLine *Chlamydia*.

The antigens CT431 and CT603 have, in addition, less cross-reactivity to *C. pneumoniae* than all the already known antigens.

EXAMPLE 5

Production of a Biochip

The antigens were applied by a contactless dispensing method (AD3050, Biodot) on an approx. 1 cm$^2$ plastic chip, consisting for example of polycarbonate or polystyrene with suitably activated surface. The distance between the individual antigen dots is 1.125 mm. A total of up to 99 antigens can be applied on the biochip. The antigens CT017, CT098, CT318-L1P, CT431, CT456-TARP, CT603-TSAP and CT664 from *Chlamydia trachomatis* are applied as antigens on the biochip. Additionally, antigens, e.g. from *Chlamydia pneumoniae* and *Chlamydia psittaci* can be applied on the biochip, in order to clarify the status of human-pathogenic chlamydia infections.

Furthermore, it is also possible to apply, additionally, e.g. antigens from the bacteria *Yersinia enterolitica, Salmonella enteritidis, Salmonella typhimurium, Campylobacter jejuni, Chlamydia trachomatis, Chlamydia pneumoniae, Borrelia burgdorferi, Streptococcus pyogenes*, the viruses Parvovirus B19 and Epstein-Barr virus and from human autoimmune antigens, in order to diagnose reactive or infectious arthritis and differentiate from autoimmune diseases. Moreover, for further questions it is possible for other antigens or combinations of these with other antigens to be applied on the biochip.

The biochip is inserted in a plastic cartridge. The plastic cartridge forms a closed system with the components: cartridge body with serum container and microfluidic channels, plastic chip with immobilized antigens, covering foil for sealing the cartridge and elastic septum for fluidic coupling to an assay processor, which pumps the necessary reagent solutions such as buffers, fluorescent dye conjugates and conditioning media into the BioChip cartridge.

In the first step of the test sequence, the serum container of the cartridge is filled with diluted serum and the cartridge with the integrated biochip is inserted in the assay processor and the serum is drawn uniformly over the dot-array. After incubation of the serum, the bound antibodies react with fluorescent dye conjugates. Both following incubation of the serum and incubation of the conjugate, a rinse cycle is applied for removing the unbound serum or conjugate residues. The fluorescence is then evaluated quantitatively by fluorescence spectrometry in a fluorescence reader. By using dye conjugates with different immunoglobulins, e.g. antihuman-IgG and antihuman-IgM, different classes of immunoglobulins, which are present in different amounts in different stages of the infection, can be detected quantitatively.

EXAMPLE 6

Execution of the Test Method with a Biochip

The test method according to the invention can also be carried out using a biochip. The method is carried out similarly to example 2, with the antigens immobilized on a biochip.

The surface of the biochip, on which the antigens are immobilized, can consist of a nitrocellulose membrane, or of activated plastic (for example polystyrene, polycarbonate, ceramic) or activated glass. Using dispensing equipment, e.g. BioDot AD3050, the antigens can also be sprayed automatically, directly onto the surface of the biochip.

Following immobilization of the antigens on the biochip, the biochips are treated with a protein-containing solution, in order to saturate still unoccupied protein binding sites on the surface of the biochip. The rest of the test procedure is similar to the processing of the nitrocellulose membrane strips, as described in example 2.

In addition to coloration with a peroxidase-labeled secondary antibody and the staining substrate TMB, the antigen-antibody reaction can also be detected with a secondary antibody, to which a fluorescent dye is conjugated. The fluorescence can then be determined in a fluorescence scanner, e.g. Tecan LS 200.

The invention claimed is:

1. A test kit for the selective detection of *Chlamydia trachomatis* infections and the serological differentiation among acute *Chlamydia pneumoniae* infection, acute *Chlamydia trachomatis* infection and chronic *Chlamydia trachomatis* infection, said kit consisting of two to seven antigens selected from the group consisting of SEQ ID NOs: 1-8, 10-15, 19-23, 25, and 28, wherein at least one of said antigens comprises a *Chlamydia trachomatis*-specific CT456-TARP antigen selected from the group consisting of SEQ ID NO: 5, SEQ ID NO: 21, SEQ ID NO: 22, SEQ ID NO:23 and SEQ ID NO: 25.

2. A method for the selective detection of *Chlamydia trachomatis* infections and the serological differentiation among acute *Chlamydia pneumoniae* infection, acute *Chlamydia trachomatis* infection and chronic *Chlamydia trachomatis* infection, said method comprising the step of detecting antibodies in a sample using the test kit of claim 8.

3. The method as claimed in claim 2, wherein said step of detecting antibodies in a sample uses at least three antigens.

4. The method as claimed in claim 2, characterized in that the method of detection of the antibodies comprises the detection of an antigen/antibody complex.

5. The method as claimed in claim 2, characterized in that the method of detection of the antibodies utilizes an ELISA (enzyme-linked immunosorbent assay) test method, Western blot or line assay.

6. A biochip for the selective detection of *Chlamydia trachomatis* infections and the serologic differentiation among acute *Chlamydia pneumoniae* infection, acute *Chlamydia trachomatis* infection and chronic *Chlamydia trachomatis* infection, said biochip comprising two to seven antigens selected from the group consisting of SEQ ID NOs: 1-8, 10-15, 19-23, 25, and 28, wherein at least one of said antigens comprises a *Chlamydia trachomatis*-specific CT456-TARP antigen selected from the group consisting of SEQ ID NO: 5, SEQ ID NO: 21, SEQ ID NO: 22, SEQ ID NO:23 and SEQ ID NO: 25.

7. The biochip as claimed in claim 6, wherein said biochip comprises CT017 (SEQ ID NO: 1), CT098 (SEQ ID NO: 2), CT318-L1P (SEQ ID NO: 3), CT431 (SEQ ID NO: 4), CT456-TARP (SEQ ID NO: 5), CT603-TSAP (SEQ ID NO: 6) and CT664 (SEQ ID NO: 7).

8. The biochip as claimed in claim 6, characterized in that the *Chlamydia trachomatis*-specific antigens are applied at a site of a membrane of the biochip, which is spatially separated from other sites on the membrane, on which other antigens are applied.

9. The biochip as claimed in claim 6, characterized in that, spatially separately from the *Chlamydia trachomatis*-specific antigens, other antigens are applied on the membrane, which permit specific detection against *Chlamydia pneumonia* or *Chlamydia pittance*.

10. A method for the selective detection of *Chlamydia trachomatis* infections and the serological differentiation among acute *Chlamydia pneumoniae* infection, acute *Chlamydia trachomatis* infection and chronic *Chlamydia trachomatis* infection, said method comprising the step of detecting antibodies in a sample using the biochip of claim 6.

* * * * *

UNITED STATES PATENT AND TRADEMARK OFFICE
CERTIFICATE OF CORRECTION

PATENT NO. : 8,455,210 B2
APPLICATION NO. : 12/527388
DATED : June 4, 2013
INVENTOR(S) : Ulrike Simnacher et al.

It is certified that error appears in the above-identified patent and that said Letters Patent is hereby corrected as shown below:

In the Claims:

On column 47, line 17 (claim 2, line 6), please replace the phrase "claim 8" with -- claim 1 --.

Signed and Sealed this
Sixteenth Day of July, 2013

Teresa Stanek Rea
*Acting Director of the United States Patent and Trademark Office*

```
SEQUENCE LISTING

<160> NUMBER OF SEQ ID NOS: 29

<210> SEQ ID NO 1
<211> LENGTH: 433
<212> TYPE: PRT
<213> ORGANISM: Chlamydia trachomatis

<400> SEQUENCE: 1

Met Leu Ile Phe Ala Leu Ser Phe Gly Ala Asp Ala Cys Leu Cys Ala
1               5                   10                  15

Ala Asp Leu Ser Lys Ala Lys Val Glu Ala Ser Val Gly Asp Arg Ala
            20                  25                  30

Ala Phe Ser Pro Phe Thr Gly Glu Ile Lys Gly Asn Arg Val Arg Leu
        35                  40                  45

Arg Leu Ala Pro His Thr Asp Ser Phe Ile Ile Lys Glu Leu Ser Lys
    50                  55                  60

Gly Asp Cys Leu Ala Val Leu Gly Glu Ser Lys Asp Tyr Tyr Val Val
65                  70                  75                  80

Ala Ala Pro Glu Gly Val Arg Gly Tyr Val Phe Arg Thr Phe Val Leu
                85                  90                  95

Asp Asn Val Ile Glu Gly Glu Lys Val Asn Val Arg Leu Glu Pro Ser
            100                 105                 110

Thr Ser Ala Pro Ile Leu Ala Arg Leu Ser Lys Gly Thr Val Val Lys
        115                 120                 125

Thr Leu Gly Ala Ala Gln Gly Lys Trp Ile Glu Ile Ala Leu Pro Lys
    130                 135                 140

Gln Cys Val Phe Tyr Val Ala Lys Asn Phe Val Lys Asn Val Gly Ala
145                 150                 155                 160

Leu Asp Leu Tyr Asn Gln Lys Glu Gly Gln Lys Lys Leu Ala Leu Asp
                165                 170                 175

Leu Leu Ser Ser Ala Met Asp Phe Ala Asp Ala Glu Leu Gln Lys Lys
            180                 185                 190

Ile Glu Asp Ile Asp Leu Asp Ala Ile Tyr Lys Lys Met Asn Leu Ala
        195                 200                 205

Gln Ser Glu Glu Phe Lys Asp Val Pro Gly Leu Gln Ser Leu Val Gln
```

```
        210                 215                 220
Lys Ala Leu Glu Arg Val Gln Glu Ala Phe Leu Ala Lys Ser Leu Glu
225                 230                 235                 240

Lys Ser Ser Val Lys Val Pro Glu Ile Arg His Lys Val Leu Glu Glu
                245                 250                 255

Ile Ala Val Val Ser Pro Ala Val Glu Glu Thr Pro Val Val Thr Lys
                260                 265                 270

Thr Glu Glu Gln Lys Val Thr Thr Val Pro Val Pro Ala Pro Ala Val
                275                 280                 285

Val Thr Glu Pro Ala Gln Asp Leu Ser Ser Val Lys Gly Ser Leu Leu
                290                 295                 300

Ser His Tyr Ile Arg Lys Lys Gly Phe Val Lys Ala Ser Pro Val Ile
305                 310                 315                 320

Glu Gly Arg Glu Ser Phe Glu Arg Ser Leu Phe Ala Val Trp Leu Ser
                325                 330                 335

Leu Gln Pro Glu Glu Ile Arg His Gln Leu Thr Met Glu Ser Phe Tyr
                340                 345                 350

Arg Asp Glu Gln Lys Lys Lys Arg Val Leu Thr Gly Glu Leu Glu Val
                355                 360                 365

Tyr Pro His Ile Val Lys Asn Asn Pro Gly Asp Tyr Leu Leu Lys Asn
                370                 375                 380

Gly Glu Asp Val Val Ala Phe Val Tyr Ala Thr Ser Ile Asp Leu Ser
385                 390                 395                 400

Lys Trp Leu Gly Lys Ser Val Val Leu Glu Cys Val Ser Arg Pro Asn
                405                 410                 415

Asn His Phe Ala Phe Pro Ala Tyr Ile Val Leu Ser Val Lys Glu Gly
                420                 425                 430

Ala

<210> SEQ ID NO 2
<211> LENGTH: 569
<212> TYPE: PRT
<213> ORGANISM: Chlamydia trachomatis

<400> SEQUENCE: 2

Met Pro Lys Gln Ala Asp Tyr Thr Trp Gly Ala Lys Lys Asn Leu Asp
1               5                   10                  15

Thr Ile Ala Cys Leu Pro Glu Asp Val Lys Gln Phe Lys Asp Leu Leu
                20                  25                  30

Tyr Ala Met Tyr Gly Phe Thr Ala Thr Glu Glu Pro Thr Ser Glu
                35                  40                  45

Val His Pro Gly Ala Ile Leu Lys Gly Thr Val Val Asp Ile Ser Lys
                50                  55                  60

Asp Phe Val Val Asp Val Gly Leu Lys Ser Glu Gly Val Ile Pro
65                  70                  75                  80

Met Ser Glu Phe Ile Asp Ser Ser Glu Gly Leu Thr Val Gly Ala Glu
                85                  90                  95

Val Glu Val Tyr Leu Asp Gln Thr Glu Asp Glu Gly Lys Val Val
                100                 105                 110

Leu Ser Arg Glu Lys Ala Thr Arg Gln Arg Gln Trp Glu Tyr Ile Leu
                115                 120                 125

Ala His Cys Glu Glu Gly Ser Ile Val Lys Gly Gln Ile Thr Arg Lys
                130                 135                 140

Val Lys Gly Gly Leu Ile Val Asp Ile Gly Met Glu Ala Phe Leu Pro
145                 150                 155                 160
```

-continued

Gly Ser Gln Ile Asp Asn Lys Lys Ile Lys Asn Leu Asp Asp Tyr Val
            165                 170                 175
Gly Lys Val Cys Glu Phe Lys Ile Leu Lys Ile Asn Val Asp Arg Arg
            180                 185                 190
Asn Val Val Ser Arg Arg Glu Leu Glu Ala Glu Arg Ile Ser
            195                 200                 205
Lys Lys Ala Glu Leu Ile Glu Gln Ile Thr Ile Gly Glu Arg Arg Lys
210                 215                 220
Gly Ile Val Lys Asn Ile Thr Asp Phe Gly Val Phe Leu Asp Leu Asp
225                 230                 235                 240
Gly Ile Asp Gly Leu Leu His Ile Thr Asp Met Thr Trp Lys Arg Ile
            245                 250                 255
Arg His Pro Ser Glu Met Val Glu Leu Asn Gln Glu Leu Glu Val Ile
            260                 265                 270
Ile Leu Ser Val Asp Lys Glu Lys Gly Arg Val Ala Leu Gly Leu Lys
            275                 280                 285
Gln Lys Glu His Asn Pro Trp Glu Asp Ile Glu Lys Lys Tyr Pro Pro
            290                 295                 300
Gly Lys Arg Val Arg Gly Lys Ile Val Lys Leu Leu Pro Tyr Gly Ala
305                 310                 315                 320
Phe Ile Glu Ile Glu Glu Gly Ile Glu Gly Leu Ile His Val Ser Glu
            325                 330                 335
Met Ser Trp Val Lys Asn Ile Val Asp Pro Asn Glu Val Val Asn Lys
            340                 345                 350
Gly Asp Glu Val Glu Val Val Leu Ser Ile Gln Lys Asp Glu Gly
            355                 360                 365
Lys Ile Ser Leu Gly Leu Lys Gln Thr Lys His Asn Pro Trp Asp Asn
370                 375                 380
Ile Glu Glu Lys Tyr Pro Ile Gly Leu Arg Val Thr Ala Glu Ile Lys
385                 390                 395                 400
Asn Leu Thr Asn Tyr Gly Ala Phe Val Glu Leu Glu Pro Gly Ile Glu
            405                 410                 415
Gly Leu Ile His Ile Ser Asp Met Ser Trp Ile Lys Lys Val Ser His
            420                 425                 430
Pro Ser Glu Leu Phe Lys Lys Gly Asn Thr Val Glu Ala Val Ile Leu
            435                 440                 445
Ser Val Asp Lys Glu Ser Lys Lys Ile Thr Leu Gly Val Lys Gln Leu
            450                 455                 460
Thr Pro Asn Pro Trp Asp Glu Ile Glu Val Met Phe Pro Val Gly Ser
465                 470                 475                 480
Asp Ile Ser Gly Val Val Thr Lys Ile Thr Ala Phe Gly Ala Phe Val
            485                 490                 495
Glu Leu Gln Asn Gly Ile Glu Gly Leu Ile His Val Ser Glu Leu Ser
            500                 505                 510
Glu Lys Pro Phe Ala Lys Ile Glu Asp Val Leu Ser Ile Gly Asp Lys
            515                 520                 525
Val Ser Ala Lys Val Ile Lys Leu Asp Pro Asp His Lys Lys Val Ser
            530                 535                 540
Leu Ser Ile Lys Glu Phe Leu Val His Gly Gly Asp Ala Gly His Asp
545                 550                 555                 560
Ala Glu Glu Glu Ser Ser Asp Arg Asp
            565

```
<210> SEQ ID NO 3
<211> LENGTH: 232
<212> TYPE: PRT
<213> ORGANISM: Chlamydia trachomatis

<400> SEQUENCE: 3

Met Thr Lys His Gly Lys Arg Ile Arg Gly Ile Gln Glu Thr Tyr Asp
1               5                   10                  15

Leu Ala Lys Ser Tyr Ser Leu Gly Glu Ala Ile Asp Ile Leu Lys Gln
                20                  25                  30

Cys Pro Thr Val Arg Phe Asp Gln Thr Val Asp Val Ser Val Lys Leu
            35                  40                  45

Gly Ile Asp Pro Arg Lys Ser Asp Gln Gln Ile Arg Gly Ser Val Ser
        50                  55                  60

Leu Pro His Gly Thr Gly Lys Val Leu Arg Ile Leu Val Phe Ala Ala
65                  70                  75                  80

Gly Asp Lys Ala Ala Glu Ala Ile Glu Ala Gly Ala Asp Phe Val Gly
                85                  90                  95

Ser Asp Asp Leu Val Glu Lys Ile Lys Gly Gly Trp Val Asp Phe Asp
            100                 105                 110

Val Ala Val Ala Thr Pro Asp Met Met Arg Glu Val Gly Lys Leu Gly
        115                 120                 125

Lys Val Leu Gly Pro Arg Asn Leu Met Pro Thr Pro Lys Ala Gly Thr
130                 135                 140

Val Thr Thr Asp Val Val Lys Thr Val Ala Glu Leu Arg Lys Gly Lys
145                 150                 155                 160

Ile Glu Phe Lys Ala Asp Arg Ala Gly Val Cys Asn Val Gly Val Ala
                165                 170                 175

Lys Leu Ser Phe Asp Ser Ala Gln Ile Lys Glu Asn Val Glu Ala Leu
            180                 185                 190

Cys Ala Ala Leu Val Lys Ala Lys Pro Ala Thr Ala Lys Gly Gln Tyr
        195                 200                 205

Leu Val Asn Phe Thr Ile Ser Ser Thr Met Gly Pro Gly Val Thr Val
    210                 215                 220

Asp Thr Arg Glu Leu Ile Ala Leu
225                 230

<210> SEQ ID NO 4
<211> LENGTH: 192
<212> TYPE: PRT
<213> ORGANISM: Chlamydia trachomatis

<400> SEQUENCE: 4

Met Pro Glu Gly Glu Met Met His Lys Leu Gln Asp Val Ile Asp Arg
1               5                   10                  15

Lys Leu Leu Asp Ser Arg Arg Ile Phe Phe Ser Glu Pro Val Thr Glu
                20                  25                  30

Lys Ser Ala Thr Glu Ala Ile Lys Lys Leu Trp Tyr Leu Glu Leu Thr
            35                  40                  45

Asn Pro Gly Gln Pro Ile Val Phe Val Ile Asn Ser Pro Gly Gly Ser
        50                  55                  60

Val Asp Ala Gly Phe Ala Val Trp Asp Gln Ile Lys Met Ile Ser Ser
65                  70                  75                  80

Pro Leu Thr Thr Val Val Thr Gly Leu Ala Ala Ser Met Gly Ser Val
                85                  90                  95

Leu Ser Leu Cys Ala Val Pro Gly Arg Arg Phe Ala Thr Pro His Ala
            100                 105                 110
```

```
Arg Ile Met Ile His Gln Pro Ser Ile Gly Gly Thr Ile Thr Gly Gln
        115                 120                 125

Ala Thr Asp Leu Asp Ile His Ala Arg Glu Ile Leu Lys Thr Lys Ala
    130                 135                 140

Arg Ile Ile Asp Val Tyr Val Glu Ala Thr Gly Gln Ser Arg Glu Val
145                 150                 155                 160

Ile Glu Lys Ala Ile Asp Arg Asp Met Trp Met Ser Ala Asn Glu Ala
                165                 170                 175

Met Glu Phe Gly Leu Leu Asp Gly Ile Leu Phe Ser Phe Asn Asp Leu
            180                 185                 190

<210> SEQ ID NO 5
<211> LENGTH: 1005
<212> TYPE: PRT
<213> ORGANISM: Chlamydia trachomatis

<400> SEQUENCE: 5

Met Thr Asn Ser Ile Ser Gly Tyr Gln Pro Thr Val Thr Thr Ser Thr
1               5                   10                  15

Ser Ser Thr Thr Ser Ala Ser Gly Ala Ser Gly Ser Leu Gly Ala Ser
            20                  25                  30

Ser Val Ser Thr Thr Ala Asn Ala Thr Val Thr Gln Thr Ala Asn Ala
        35                  40                  45

Thr Asn Ser Ala Ala Thr Ser Ser Ile Gln Thr Thr Gly Glu Thr Val
    50                  55                  60

Val Asn Tyr Thr Asn Ser Ala Ser Ala Pro Asn Val Thr Val Ser Thr
65                  70                  75                  80

Ser Ser Ser Ser Thr Gln Ala Thr Ala Thr Ser Asn Lys Thr Ser Gln
                85                  90                  95

Ala Val Ala Gly Lys Ile Thr Ser Pro Asp Thr Ser Glu Ser Ser Glu
            100                 105                 110

Thr Ser Ser Thr Ser Ser Ser Asp His Ile Pro Ser Asp Tyr Asp Asp
        115                 120                 125

Val Gly Ser Asn Ser Gly Asp Ile Ser Asn Asn Tyr Asp Asp Val Gly
    130                 135                 140

Ser Asn Asn Gly Asp Ile Ser Ser Asn Tyr Asp Asp Ala Ala Ala Asp
145                 150                 155                 160

Tyr Glu Pro Ile Arg Thr Thr Glu Asn Ile Tyr Glu Ser Ile Gly Gly
                165                 170                 175

Ser Arg Thr Ser Gly Pro Glu Asn Thr Ser Gly Gly Ala Ala Ala Ala
            180                 185                 190

Leu Asn Ser Leu Arg Gly Ser Ser Tyr Ser Asn Tyr Asp Asp Ala Ala
        195                 200                 205

Ala Asp Tyr Glu Pro Ile Arg Thr Thr Glu Asn Ile Tyr Glu Ser Ile
    210                 215                 220

Gly Gly Ser Arg Thr Ser Gly Pro Glu Asn Thr Ser Gly Gly Ala Ala
225                 230                 235                 240

Ala Ala Leu Asn Ser Leu Arg Gly Ser Ser Tyr Ser Asn Tyr Asp Asp
                245                 250                 255

Ala Ala Ala Asp Tyr Glu Pro Ile Arg Thr Thr Glu Asn Ile Tyr Glu
            260                 265                 270

Ser Ile Gly Gly Ser Arg Thr Ser Gly Pro Glu Asn Thr Ser Asp Gly
        275                 280                 285

Ala Ala Ala Ala Ala Leu Asn Ser Leu Arg Gly Ser Ser Tyr Thr Thr
    290                 295                 300
```

-continued

```
Gly Pro Arg Asn Glu Gly Val Phe Gly Pro Gly Pro Glu Gly Leu Pro
305                 310                 315                 320

Asp Met Ser Leu Pro Ser Tyr Asp Pro Thr Asn Lys Thr Ser Leu Leu
            325                 330                 335

Thr Phe Leu Ser Asn Pro His Val Lys Ser Lys Met Leu Glu Asn Ser
            340                 345                 350

Gly His Phe Val Phe Ile Asp Thr Asp Arg Ser Ser Phe Ile Leu Val
            355                 360                 365

Pro Asn Gly Asn Trp Asp Gln Val Cys Ser Ile Lys Val Gln Asn Gly
            370                 375                 380

Lys Thr Lys Glu Asp Leu Asp Ile Lys Asp Leu Glu Asn Met Cys Ala
385                 390                 395                 400

Lys Phe Cys Thr Gly Phe Ser Lys Phe Ser Gly Asp Trp Asp Ser Leu
            405                 410                 415

Val Glu Pro Met Val Ser Ala Lys Ala Gly Val Ala Ser Gly Gly Asn
            420                 425                 430

Leu Pro Asn Thr Val Ile Ile Asn Asn Lys Phe Lys Thr Cys Val Ala
            435                 440                 445

Tyr Gly Pro Trp Asn Ser Gln Glu Ala Ser Ser Gly Tyr Thr Pro Ser
            450                 455                 460

Ala Trp Arg Arg Gly His Arg Val Asp Phe Gly Gly Ile Phe Glu Lys
465                 470                 475                 480

Ala Asn Asp Phe Asn Lys Ile Asn Trp Gly Thr Gln Ala Gly Pro Ser
            485                 490                 495

Ser Glu Asp Asp Gly Ile Ser Phe Ser Asn Glu Thr Pro Gly Ala Gly
            500                 505                 510

Pro Ala Ala Ala Pro Ser Pro Thr Pro Ser Ser Ile Pro Ile Ile Asn
            515                 520                 525

Val Asn Val Asn Val Gly Gly Thr Asn Val Asn Ile Gly Asp Thr Asn
            530                 535                 540

Val Asn Thr Thr Asn Thr Thr Pro Thr Thr Gln Ser Thr Asp Ala Ser
545                 550                 555                 560

Thr Asp Thr Ser Asp Ile Asp Asp Ile Asn Thr Asn Asn Gln Thr Asp
            565                 570                 575

Asp Ile Asn Thr Thr Asp Lys Asp Ser Asp Gly Ala Gly Gly Val Asn
            580                 585                 590

Gly Asp Ile Ser Glu Thr Glu Ser Ser Gly Asp Ser Gly Ser
            595                 600                 605

Val Ser Ser Ser Glu Ser Asp Lys Asn Ala Ser Val Gly Asn Asp Gly
610                 615                 620

Pro Ala Met Lys Asp Ile Leu Ser Ala Val Arg Lys His Leu Asp Val
625                 630                 635                 640

Val Tyr Pro Gly Glu Asn Gly Ser Thr Glu Gly Pro Leu Pro Ala
            645                 650                 655

Asn Gln Thr Leu Gly Asp Val Ile Ser Asp Val Glu Asn Lys Gly Ser
            660                 665                 670

Ala Gln Asp Thr Lys Leu Ser Gly Asn Thr Gly Ala Gly Asp Asp Asp
            675                 680                 685

Pro Thr Thr Thr Ala Ala Val Gly Asn Gly Ala Glu Glu Ile Thr Leu
            690                 695                 700

Ser Asp Thr Asp Ser Gly Ile Gly Asp Asp Val Ser Asp Thr Ala Ser
705                 710                 715                 720

Ser Ser Gly Asp Glu Ser Gly Gly Val Ser Ser Pro Ser Ser Glu Ser
```

```
                        725                 730                 735
Asn Lys Asn Thr Ala Val Gly Asn Asp Gly Pro Ser Gly Leu Asp Ile
        740                 745                 750

Leu Ala Ala Val Arg Lys His Leu Asp Lys Val Tyr Pro Gly Asp Asn
        755                 760                 765

Gly Gly Ser Thr Glu Gly Pro Leu Gln Ala Asn Gln Thr Leu Gly Asp
        770                 775                 780

Ile Val Gln Asp Met Glu Thr Thr Gly Thr Ser Gln Glu Thr Val Val
785                 790                 795                 800

Ser Pro Trp Lys Gly Ser Thr Ser Thr Glu Ser Ala Gly Gly Ser
                    805                 810                 815

Gly Ser Val Gln Thr Leu Leu Pro Ser Pro Pro Thr Pro Ser Thr
        820                 825                 830

Thr Thr Leu Arg Thr Gly Thr Gly Ala Thr Thr Thr Ser Leu Met Met
        835                 840                 845

Gly Gly Pro Ile Lys Ala Asp Ile Ile Thr Thr Gly Gly Gly Arg
        850                 855                 860

Ile Pro Gly Gly Gly Thr Leu Glu Lys Leu Leu Pro Arg Ile Arg Ala
865                 870                 875                 880

His Leu Asp Ile Ser Phe Asp Ala Gln Gly Asp Leu Val Ser Thr Glu
                    885                 890                 895

Glu Pro Gln Leu Gly Ser Ile Val Asn Lys Phe Arg Gln Glu Thr Gly
        900                 905                 910

Ser Arg Gly Ile Leu Ala Phe Val Glu Ser Ala Pro Gly Lys Pro Gly
        915                 920                 925

Ser Ala Gln Val Leu Thr Gly Thr Gly Gly Asp Lys Gly Asn Leu Phe
        930                 935                 940

Gln Ala Ala Ala Ala Val Thr Gln Ala Leu Gly Asn Val Ala Gly Lys
945                 950                 955                 960

Val Asn Leu Ala Ile Gln Gly Gln Lys Leu Ser Ser Leu Val Asn Asp
                    965                 970                 975

Asp Gly Lys Gly Ser Val Gly Arg Asp Leu Phe Gln Ala Ala Ala Gln
        980                 985                 990

Thr Thr Gln Val Leu Ser Ala Leu Ile Asp Thr Val Gly
        995                 1000                1005

<210> SEQ ID NO 6
<211> LENGTH: 195
<212> TYPE: PRT
<213> ORGANISM: Chlamydia trachomatis

<400> SEQUENCE: 6

Met Gly Ser Leu Val Gly Arg Gln Ala Pro Asp Phe Ser Gly Lys Ala
1               5                   10                  15

Val Val Cys Gly Glu Glu Lys Glu Ile Ser Leu Ala Asp Phe Arg Gly
                20                  25                  30

Lys Tyr Val Val Leu Phe Phe Tyr Pro Lys Asp Phe Thr Tyr Val Cys
            35                  40                  45

Pro Thr Glu Leu His Ala Phe Gln Asp Arg Leu Val Asp Phe Glu Glu
        50                  55                  60

Arg Gly Ala Val Val Leu Gly Cys Ser Val Asp Asp Ile Glu Thr His
65                  70                  75                  80

Ser Arg Trp Leu Ala Val Ala Arg Asn Ala Gly Gly Ile Glu Gly Thr
                85                  90                  95

Glu Tyr Pro Leu Leu Ala Asp Pro Ser Phe Lys Ile Ser Glu Ala Phe
```

```
                   100                 105                 110
Gly Val Leu Asn Pro Glu Gly Ser Leu Ala Leu Arg Ala Thr Phe Leu
        115                 120                 125

Ile Asp Lys Tyr Gly Val Val Arg His Ala Val Ile Asn Asp Leu Pro
130                 135                 140

Leu Gly Arg Ser Ile Asp Glu Glu Leu Arg Ile Leu Asp Ser Leu Ile
145                 150                 155                 160

Phe Phe Glu Asn His Gly Met Val Cys Pro Ala Asn Trp Arg Ser Gly
                165                 170                 175

Glu Arg Gly Met Val Pro Ser Glu Glu Gly Leu Lys Glu Tyr Phe Gln
            180                 185                 190

Thr Met Asp
        195

<210> SEQ ID NO 7
<211> LENGTH: 829
<212> TYPE: PRT
<213> ORGANISM: Chlamydia trachomatis

<400> SEQUENCE: 7

Met Gly Ile Arg Leu Val Ile Asp Lys Gly Pro Leu Ser Gly Thr Val
1               5                   10                  15

Leu Ile Leu Glu Asn Gly Thr Ser Trp Ser Leu Gly Ser Asp Gly Lys
            20                  25                  30

Ala Ser Asp Ile Leu Leu Gln Asp Glu Lys Leu Ala Pro Ser Gln Ile
        35                  40                  45

Arg Ile Thr Leu Lys Asp Gly Glu Tyr Tyr Leu Glu Asn Leu Asp Ala
    50                  55                  60

Leu Arg Pro Val Ser Val Asp Gly Thr Val Ile Thr Ala Pro Val Leu
65                  70                  75                  80

Leu Lys Asp Gly Val Ser Phe Val Met Gly Ser Cys Gln Val Ser Phe
                85                  90                  95

Phe Lys Gly Glu Glu Val Glu Gly Asp Ile Glu Leu Ser Phe Gln Thr
            100                 105                 110

Glu Gly Gly Asn Glu Gly Glu Pro Ala Ala Gln Gly Ser Ser Ser Val
        115                 120                 125

Ser Ser Glu Ala Pro Lys Lys Glu Thr Gly Asn Pro Ser Leu Pro Ser
130                 135                 140

Glu Ala Lys Ala Ser Gly Glu Val Ser Ser Ala Ile Ala Lys Glu
145                 150                 155                 160

Gln Glu Leu Ala Ala Ser Phe Leu Ala Ser Val Glu Lys Glu Pro Gly
                165                 170                 175

Thr Pro Lys Glu Val Ser Glu Pro Lys Val Ser Ser Gln Glu Gly Gln
            180                 185                 190

Thr Pro Ser Val Thr Gly Glu Lys Lys Asp Leu Glu Leu Pro Leu Ala
        195                 200                 205

Ser Gln Glu Gln Pro Lys Gln Thr Thr Pro Ser Gly Ser Gly Glu Pro
210                 215                 220

Thr Gln Ser Gln Asn Ala Ser Met Glu Glu Asn Arg Thr Ser Pro Asp
225                 230                 235                 240

Gln Asn Gln Gln Pro Gln Leu Ser Ser Ala Ser Glu Ser Gly Ser Gln
                245                 250                 255

Ser Pro Glu Asn Gln Glu Gln Pro Ser Gln Thr Pro Pro Pro Ser
            260                 265                 270

Pro Glu Thr Pro Glu Pro Ser Gly Glu Pro Asn Ser Ala Thr Glu Glu
```

```
            275                 280                 285
Asn Ser Pro Ser Pro Met Glu Lys Ala Ser Val Thr Glu Glu Gly Ser
290                 295                 300
Ser Gly Thr Ser Glu Glu Lys Glu Gly Glu Asp Thr Ala Glu
305                 310                 315                 320
Ser Ala Ala Asn Glu Glu Pro Lys Ala Glu Ala Ser Gln Glu Glu Glu
                325                 330                 335
Lys Lys Glu Glu Asp Lys Gly Glu Val Leu Ala Pro Phe Asn Val Gln
            340                 345                 350
Asp Leu Phe Arg Phe Asp Gln Gly Ile Phe Pro Ala Glu Ile Glu Asp
            355                 360                 365
Leu Ala Gln Lys Gln Val Ala Val Asp Leu Thr Gln Pro Ser Arg Phe
    370                 375                 380
Leu Leu Lys Val Leu Ala Gly Ala Asn Ile Gly Ala Glu Phe His Leu
385                 390                 395                 400
Asp Ser Gly Lys Thr Tyr Ile Val Gly Ser Asp Pro Gln Val Ala Asp
                405                 410                 415
Ile Val Leu Ser Asp Met Ser Ile Ser Arg Gln His Ala Lys Ile Ile
            420                 425                 430
Ile Gly Asn Asp Asn Ser Val Leu Ile Glu Asp Leu Gly Ser Lys Asn
            435                 440                 445
Gly Val Ile Val Glu Gly Arg Lys Ile Glu His Gln Ser Thr Leu Ser
    450                 455                 460
Ala Asn Gln Val Val Ala Leu Gly Thr Thr Leu Phe Leu Leu Val Asp
465                 470                 475                 480
Tyr Ala Ala Pro Ser Asp Thr Val Met Ala Thr Ile Ser Ser Glu Asp
                485                 490                 495
Tyr Gly Leu Phe Gly Arg Pro Gln Ser Pro Glu Glu Ile Ala Ala Arg
            500                 505                 510
Ala Ala Glu Glu Glu Glu Lys Arg Lys Arg Ala Thr Leu Pro Thr
            515                 520                 525
Gly Ala Phe Ile Leu Thr Leu Phe Ile Gly Gly Leu Ala Leu Leu Phe
    530                 535                 540
Gly Ile Gly Thr Ala Ser Leu Phe His Thr Lys Glu Val Val Ser Ile
545                 550                 555                 560
Asp Gln Ile Asp Leu Ile His Asp Ile Glu His Val Ile Gln Gln Phe
                565                 570                 575
Pro Thr Val Arg Phe Thr Phe Asn Lys Asn Asn Gly Gln Leu Phe Leu
            580                 585                 590
Ile Gly His Val Arg Asn Ser Ile Asp Lys Ser Glu Leu Leu Tyr Lys
            595                 600                 605
Val Asp Ala Leu Ser Phe Val Lys Ser Val Asp Asp Asn Val Ile Asp
    610                 615                 620
Asp Glu Ala Val Trp Gln Glu Met Asn Ile Leu Leu Ser Lys Asn Pro
625                 630                 635                 640
Glu Phe Lys Gly Ile Ser Met Gln Ser Pro Glu Pro Gly Ile Phe Val
                645                 650                 655
Ile Ser Gly Tyr Leu Lys Thr Glu Glu Gln Ala Ala Cys Leu Ala Asp
            660                 665                 670
Tyr Leu Asn Leu His Phe Asn Tyr Leu Ser Leu Leu Asp Asn Lys Val
            675                 680                 685
Ile Ile Glu Ser Gln Val Met Lys Ala Leu Ala Gly His Leu Val Gln
    690                 695                 700
```

-continued

```
Ser Gly Phe Ala Asn Val His Val Ser Phe Thr Asn Gly Glu Ala Val
705                 710                 715                 720

Leu Thr Gly Tyr Ile Asn Asn Lys Asp Ala Asp Lys Phe Arg Thr Val
                725                 730                 735

Val Gln Glu Leu Gln Asp Ile Ala Gly Ile Arg Ala Val Lys Asn Phe
            740                 745                 750

Val Val Leu Leu Pro Ala Glu Glu Gly Val Ile Asp Leu Asn Met Arg
        755                 760                 765

Tyr Pro Gly Arg Tyr Arg Val Thr Gly Phe Ser Lys Cys Gly Asp Ile
    770                 775                 780

Ser Ile Asn Val Val Asn Gly Arg Ile Leu Thr Arg Gly Asp Ile
785                 790                 795                 800

Leu Asp Gly Met Thr Val Thr Ser Ile Gln Ser His Cys Ile Phe Leu
                805                 810                 815

Glu Arg Glu Gly Leu Lys Tyr Lys Ile Glu Tyr Asn Lys
            820                 825

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Ala Val Glu Glu Thr Pro Val Val Thr Lys Thr Glu Glu Gln Lys
1               5                   10                  15

Val Thr Thr Val
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Glu Ser Phe Tyr Arg Asp Glu Gln Lys Lys Lys Arg Val Leu Thr
1               5                   10                  15

Gly Glu Leu Glu
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Tyr Pro His Ile Val Lys Asn Asn Pro Gly Asp Tyr Leu Leu Lys
1               5                   10                  15

Asn Gly Glu Asp
            20

<210> SEQ ID NO 11
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Ser Gln Ile Asp Asn Lys Lys Ile Lys Asn Leu Asp Asp Tyr Val Gly
1               5                   10                  15

Lys Val Cys Glu
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Trp Lys Arg Ile Arg His Pro Ser Glu Met Val Glu Leu Asn Gln
1               5                   10                  15

Glu Leu Glu Val
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Lys Glu His Asn Pro Trp Glu Asp Ile Glu Lys Lys Tyr Pro Pro
1               5                   10                  15

Gly Lys Arg Val
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Leu Val His Gly Gly Asp Ala Gly His Asp Ala Glu Glu Glu Ser
1               5                   10                  15

Ser Asp Arg Asp
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Thr Lys His Gly Lys Arg Ile Arg Gly Ile Gln Glu Thr Tyr Asp
1               5                   10                  15

Leu Ala Lys Ser
            20
```

-continued

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Asp Pro Arg Lys Ser Asp Gln Gln Ile Arg Gly Ser Val Ser Leu
1               5                   10                  15

Pro His Gly Thr
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Thr Pro Lys Ala Gly Thr Val Thr Thr Asp Val Val Lys Thr Val
1               5                   10                  15

Ala Glu Leu Arg
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Met Met His Lys Leu Gln Asp Val Ile Asp Arg Lys Leu Leu Asp
1               5                   10                  15

Ser Arg Arg Ile
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Val Pro Gly Arg Arg Phe Ala Thr Pro His Ala Arg Ile Met Ile
1               5                   10                  15

His Gln Pro Ser
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Ala Thr Gly Gln Ser Arg Glu Val Ile Glu Lys Ala Ile Asp Arg

```
1               5                   10                  15
Asp Met Trp Met
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ser Pro Asp Thr Ser Glu Ser Ser Glu Thr Ser Thr Ser Ser
1               5                   10                  15

Ser Asp His Ile
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ile Gly Gly Ser Arg Thr Ser Gly Pro Glu Asn Thr Ser Asp Gly
1               5                   10                  15

Ala Ala Ala Ala
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gln Glu Ala Ser Ser Gly Tyr Thr Pro Ser Ala Trp Arg Arg Gly
1               5                   10                  15

His Arg Val Asp
            20

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Asn Thr Asn Asn Gln Thr Asp Asp Ile Asn Thr Thr Asp Lys Asp
1               5                   10                  15

Ser Asp Gly Ala
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 25

Thr Glu Ser Ser Ser Gly Asp Asp Ser Gly Ser Val Ser Ser Ser Glu
1               5                   10                  15

Ser Asp Lys Asn
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ser Gly Asp Glu Ser Gly Gly Val Ser Ser Pro Ser Ser Glu Ser
1               5                   10                  15

Asn Lys Asn Thr
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Arg Gln Ala Pro Asp Phe Ser Gly Lys Ala Val Val Cys Gly Glu
1               5                   10                  15

Glu Lys Glu Ile
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Arg Asn Ala Gly Gly Ile Glu Gly Thr Glu Tyr Pro Leu Leu Ala
1               5                   10                  15

Asp Pro Ser Phe
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Trp Arg Ser Gly Glu Arg Gly Met Val Pro Ser Glu Glu Gly Leu
1               5                   10                  15

Lys Glu Tyr Phe
            20